(12) United States Patent
Jolly et al.

(10) Patent No.: US 9,622,775 B2
(45) Date of Patent: Apr. 18, 2017

(54) METHODS AND INSTRUMENTS FOR FORMING A POSTERIOR KNEE PORTAL AND FOR INSERTING A CANNULA

(71) Applicant: Arthrex, Inc., Naples, FL (US)

(72) Inventors: Jacob A. Jolly, Naples, FL (US); Joel L. Boyd, Bloomington, MN (US); Ricardo Albertorio, Naples, FL (US)

(73) Assignee: ARTHREX, INC., Naples, FL (US)

( * ) Notice: Subject to any disclaimer, the term of this patent is extended or adjusted under 35 U.S.C. 154(b) by 209 days.

(21) Appl. No.: 14/056,296

(22) Filed: Oct. 17, 2013

(65) Prior Publication Data

US 2014/0114367 A1    Apr. 24, 2014

Related U.S. Application Data

(60) Provisional application No. 61/717,948, filed on Oct. 24, 2012.

(51) Int. Cl.

| | | |
|---|---|---|
| *A61B 17/04* | (2006.01) | |
| *A61B 17/34* | (2006.01) | |
| *A61B 17/56* | (2006.01) | |
| *A61F 2/08* | (2006.01) | |
| *A61B 17/17* | (2006.01) | |
| *A61B 17/02* | (2006.01) | |
| *A61B 17/3209* | (2006.01) | |
| *A61B 17/32* | (2006.01) | |

(52) U.S. Cl.
CPC ........ *A61B 17/3423* (2013.01); *A61B 17/025* (2013.01); *A61B 17/0485* (2013.01); *A61B 17/1764* (2013.01); *A61B 17/32093* (2013.01); *A61B 17/3421* (2013.01); *A61B 17/3431* (2013.01); *A61B 17/56* (2013.01); *A61F 2/0805* (2013.01); *A61B 17/1796* (2013.01); *A61B 2017/0268* (2013.01); *A61B 2017/320044* (2013.01); *A61B 2017/320056* (2013.01); *A61B 2017/3419* (2013.01); *A61B 2017/3441* (2013.01); *A61B 2017/3458* (2013.01)

(58) Field of Classification Search
CPC ...................... A61B 17/3421; A61B 2017/047
See application file for complete search history.

(56) References Cited

U.S. PATENT DOCUMENTS

| | | | |
|---|---|---|---|
| 4,172,458 A | * | 10/1979 | Pereyra ............ A61B 17/12009 606/144 |
| 4,509,516 A | | 4/1985 | Richmond |
| 5,520,693 A | | 5/1996 | McGuire et al. |

(Continued)

FOREIGN PATENT DOCUMENTS

WO    WO 2004/075730 A2    9/2004

*Primary Examiner* — David Bates
*Assistant Examiner* — Olivia C Chang
(74) *Attorney, Agent, or Firm* — Carlson, Gaskey & Olds

(57) ABSTRACT

A specialized obturator that has a curved configuration designed specifically for entry through the anterior joint and out the back of the knee in the ideal position for a posterior portal. The curved obturator is shaped to avoid intact knee ligaments and femoral condyles. The obturator is provided with an eyelet located at the tip and may be employed with a cannula similar to a PassPort™ Button cannula, but with one or more sutures placed through the "neck" behind the collar. A standard "inside-out" cannula may be used as well, but dimensioned for the specialized obturator.

16 Claims, 7 Drawing Sheets

(56) References Cited

U.S. PATENT DOCUMENTS

| | | | |
|---|---|---|---|
| 6,161,543 A * | 12/2000 | Cox | A61B 17/00234 |
| | | | 128/898 |
| 6,626,910 B1 | 9/2003 | Hugues | |
| 6,716,234 B2 | 4/2004 | Grafton et al. | |
| 8,038,652 B2 | 10/2011 | Morrison et al. | |
| 2002/0055748 A1 * | 5/2002 | Gellman | A61B 17/00234 |
| | | | 606/139 |
| 2003/0212305 A1 * | 11/2003 | Anderson | A61B 17/0401 |
| | | | 600/29 |
| 2013/0035692 A1 * | 2/2013 | Sorensen | A61B 17/0401 |
| | | | 606/87 |

* cited by examiner

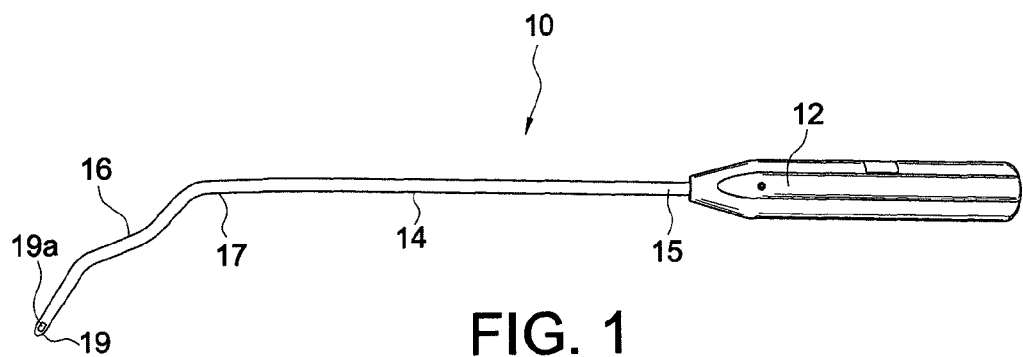
FIG. 1
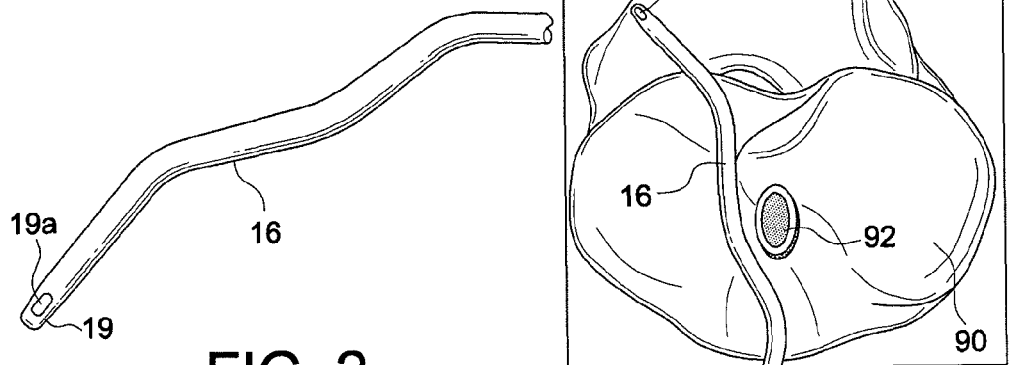
FIG. 2
FIG. 3
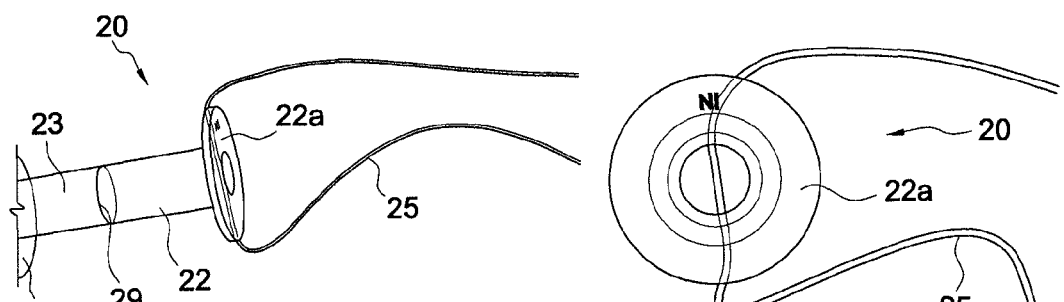
FIG. 4
FIG. 5

METHODS AND INSTRUMENTS FOR FORMING A POSTERIOR KNEE PORTAL AND FOR INSERTING A CANNULA

CROSS-REFERENCE TO RELATED APPLICATIONS

This application claims the benefit of U.S. Provisional Application No. 61/717,948 filed Oct. 24, 2012, the disclosure of which is incorporated by reference in its entirety herein.

FIELD OF THE INVENTION

The present invention relates to surgical devices and, in particular, to devices and methods for arthroscopic surgeries.

BACKGROUND OF THE INVENTION

A posterior portal is often needed during arthroscopic knee surgery for loose body removal, PCL reconstruction and meniscal repairs, among others. The standard technique involves placing a needle from outside into the joint while visualizing the entry point with the arthroscope. This step is essentially a "blind" passage of a sharp needle into the back of the knee which can pose danger to structures and often requires many attempts to get the correct position. Also, once the position is found with the needle, the surgeon must remove the needle and try to emulate that same position/direction with a scalpel blade. This is, again, another "blind" attempt to enter the joint with a sharp instrument. Subsequently, the surgeon often places a cannula from outside in, through the incision which can be difficult to do because of the thick, fibrous tissue planes of the skin, capsule, etc.

There is a need for specialized instruments that are specifically designed to allow entry through the anterior joint and out the back of the knee in the ideal position for a posterior portal. Also needed are surgical arthroscopic techniques where instruments are placed through an anterior portal, through the joint and out the posterior-medial or posterior-lateral side, so that the tip of the instrument can be seen and palpated through the skin, to further indicate the proper position for the portal.

SUMMARY OF THE INVENTION

The present invention fulfills the above needs and objectives by providing a specialized obturator that has a curved configuration designed specifically for entry through the anterior joint and out the back of the knee in the ideal position for a posterior portal. The obturator can also be shaped to avoid intact knee ligaments and condyles. The obturator is provided with an eyelet located at the tip.

The present invention can be used to insert into the knee a cannula similar to a PassPort™ Button cannula, but with one or more sutures placed through the "neck" behind the collar. A standard "inside-out" cannula may be used as well, but dimensioned for the specialized obturator.

The present invention also provides improved surgical techniques for arthroscopic procedures. A specifically-designed, curved obturator is placed through an anterior or medial portal, passing through the joint and out the posterior-medial or posterior-lateral side. The tip of the obturator can be seen and palpated through the skin, to indicate the proper position for the portal. A cutting instrument (such as a scalpel, for example) can then be used to make an incision over the tip of the oburator to make the posterior portal. The tip of the obturator is then exposed, and the eyelet can be used to pull in at least one suture attached to a cannula (for example, an Arthrex PassPort™ Button cannula, described in U.S. Pat. No. 8,038,652) through the knee and out the anterior portal. The suture is then pulled to "drag" the cannula into the knee.

Other features and advantages of the present invention will become apparent from the following description of the invention.

BRIEF DESCRIPTION OF THE DRAWINGS

FIG. 1 illustrates a perspective view of an obturator of the present invention (with a tapered eyelet tip and a curvature that allows intraarticular passage past the knee cruciate ligaments).

FIG. 2 is an enlarged view of the distal end of the obturator of FIG. 1.

FIG. 3 is a schematic top view of the distal end of the obturator shown in FIG. 2 and illustrating how the obturator is inserted around the curvature of the femoral condyle.

FIG. 4 illustrates a perspective view of a PassPort™ Button cannula with suture passed through a "neck" for use with the obturator of the present invention.

FIG. 5 is a top view of the cannula of FIG. 4.

DETAILED DESCRIPTION OF THE EMBODIMENTS

Figure 6:
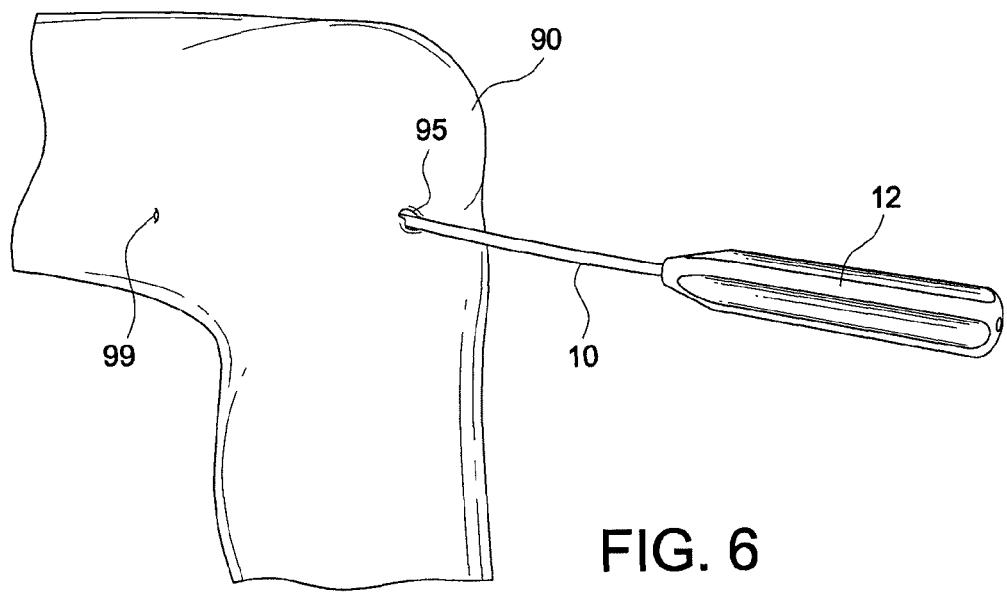
FIGS. 6-12 illustrate subsequent steps of a method of forming a posterior knee portal and passage for a cannula (such as the cannula of FIGS. 4 and 5) with the obturator of FIGS. 1-3 and according to an exemplary embodiment of the present invention.

The present invention provides a plurality of improved surgical instruments and kits configured to allow formation of a posterior portal (via entry through the anterior joint and out the back of the knee in the ideal position for a posterior portal). The instruments include a specialized obturator that is curved specifically for entry through the anterior or medial joint and out the back of the knee (to delineate the ideal position/location for a posterior portal). The obturator is shaped to avoid intact knee ligaments, condyles etc., and to follow the curvature of the medial and lateral femoral condyles. In addition to the curved shape, the obturator is also provided with an eyelet at the tip of the device. The obturator can be used to insert a cannula similar to the PassPort™ Button cannula but with at least one suture placed through the "neck" behind the collar. The obturator can also be used to insert (in lieu of the PassPort™ Button cannula) a standard "inside-out" cannula, but dimensioned for the specialized obturator.

The present invention also provides surgical arthroscopic techniques wherein specialized, improved instruments are placed through an anterior portal, through the joint and out the posterior-medial or posterior-lateral side, so that the tip of the instruments can be seen and palpated through the skin, to further indicate the proper position for the portal.

An exemplary method of forming a posterior knee portal comprises inter alia the steps of: (i) placing a specifically-shaped obturator through an anterior or medial portal, through the joint and out the posterior-medial or posterior-lateral side of the knee (so that the tip of the obturator can be seen and palpated through the skin, to indicate the proper position for the posterior portal); (ii) employing a cutting instrument to make an incision over the tip of the obturator to indicate the posterior knee portal; and (iii) exposing the tip of the obturator at the posterior knee portal.

Another exemplary method of forming a posterior knee portal and passing a cannula comprises inter alia the steps of: (i) placing a specifically-shaped, curved obturator through an anterior or medial portal, through the joint and out the posterior-medial or posterior-lateral side of the knee (so that the tip of the obturator can be seen and palpated through the skin, to indicate the proper position for the posterior portal); (ii) employing a cutting instrument such as a scalpel to make an incision over the tip of the obturator to make the portal; (iii) exposing the tip of the obturator; (iv) passing at least one flexible strand attached to a PassPort™ Button cannula through the eyelet of the exposed obturator tip; (v) pulling the obturator out of the anterior or medial portal; and (vi) pulling the flexible strand to "drag" the cannula into the knee and to position the cannula into the posterior portal.

Referring now to the drawings, where like elements are designated by like reference numerals, FIGS. 1-3 illustrate an exemplary obturator 10 of the present invention employed for the formation of a posterior arthroscopic portal (via entry through the anterior joint and out the back of the knee in the ideal position for a posterior portal). FIGS. 4 and 5 illustrate an improved cannula 20 of the present invention (i.e., a modified PassPort™ Button cannula) with suture passed through a "neck" of the cannula, for use with the obturator of FIGS. 1-3. FIGS. 6-13 illustrate subsequent steps of a method of forming a posterior knee portal with obturator 10 of FIGS. 1-3 (through the anterior knee portal) and placing/positioning cannula 20 of FIGS. 4 and 5 into the formed portal. FIGS. 14-26 illustrate subsequent steps of a method of forming a posterior knee portal with obturator 10 of FIGS. 1-3 (through the medial knee portal) and placing/positioning cannula 120 or cannula 220 (FIGS. 20 and 21) into the formed portal.

Obturator 10 is provided with a handle 12 and a shaft 14 with a proximal end 15 and a distal end 17. As shown in FIG. 1, shaft 14 is substantially straight. A curved region 16 (curved shaft 16 or curved portion 16) is provided at the distal end 17 of the straight shaft 14 (straight portion 14), as shown in FIGS. 1-3. The straight portion 14 has a length about twice the length of the curved portion 16.

Shaft 16 (curved portion 16) has a specifically curved configuration that follows the anatomy of the knee structures when the obturator is inserted through an anterior or medial portal (in the anterior or medial joint, respectively) and out the back of the knee to indicate the ideal location/position for a posterior portal. Shaft 16 (curved portion 16) is also shaped to avoid knee structures (such as knee ligaments and condyles, for example) and to preserve these structures intact during insertion into the knee joint. When inserted into the knee joint, the tip of the obturator 10 is placed around the femoral condyle and against the capsule until the tip can be palpated or seen under the skin.

The curvature of the shaft 16 allows intraarticular passage past the knee cruciate ligaments. The unique curvature of the substantially curved portion 16 fits around the cruciate ligaments and around the back of the medial and lateral femoral condyles and against the capsule. For example, FIG. 3 shows an intact ACL 92 (illustrated for simplicity by an oval structure) adjacent curved shaft 16 of obturator 10 of the present invention.

Obturator 10 is also provided with an eyelet 19a located at a tapered tip 19 (i.e., a most distal end) of the curved region 16. Eyelet 19a allows passage of flexible strand such as suture (attached to a cannula or an instrument) and subsequent cannula/instrument insertion into a portal.

Reference is now made to FIGS. 4 and 5 which illustrate exemplary cannula 20 which can be inserted using the obturator of the present invention, which is a modified Arthrex PassPort™ Button cannula 22. A PassPort™ Button cannula is detailed and described in U.S. Pat. No. 8,038,652 issued on Oct. 18, 2011, the disclosure of which is incorporated by reference in its entirety herewith. Flexible strand 25 (suture 25) is passed through neck region 22a of cannula 22 for use with obturator 10, as detailed below.

As detailed in U.S. Pat. No. 8,038,652, PassPort™ Button cannula 22 is provided with an elongated, cylindrical flexible body 23, inner and outer deformable flanges or lips 22a, 22b for improved stability when installed into the body, and at least one dam 29 to prevent fluid from squirting out of the body. PassPort™ Button cannula 22 may be manufactured from a flexible material (e.g., silicone) which enables the cannula to be deformed and or otherwise condensed in size and inserted into an insertion tool or knee portal such as posterior knee portal 100 of the present invention. The deformable flanges 22a, 22b may have a circular or oval configuration, and a diameter substantially greater than the diameter of the elongated body 23.

FIGS. 4 and 5 show strand 25 passed through the elongated body 23 or through one of the two deformable flanges, for example, through flange 22a of the PassPort™ Button cannula 22. In an exemplary embodiment, the flexible strand 25 is passed so that the strand exits at two locations about diametrically opposite to each other on the body 23 located at a neck portion adjacent flange 22a (as shown in FIG. 5).

FIGS. 6-13 illustrate steps of a method for posterior knee portal creation and cannula passage (such as cannula 20 of FIGS. 4 and 5) with the obturator 10 of FIGS. 1-3.

FIG. 6: Device 10 (obturator 10) is placed through the anterior knee portal 95 and through the joint, until the tapered tip 19 can be palpated under the skin in the area 99 of the posterior portal.

Figure 7:
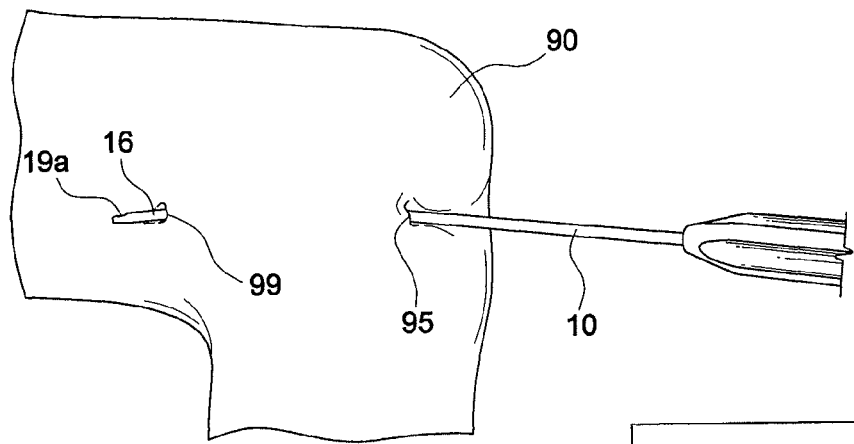
Figure 8:
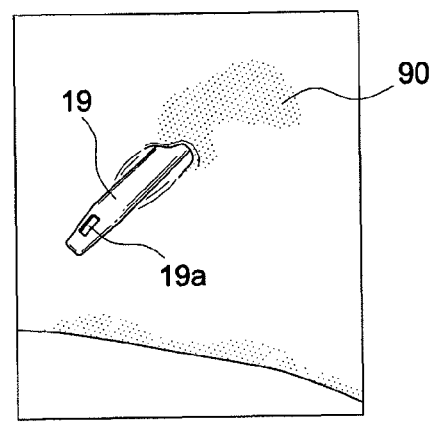

FIGS. 7 and 8: An incision is made over the tip 19 of the obturator 10 and the obturator 10 is pushed through the skin exposing the eyelet 19a.

Figure 9:
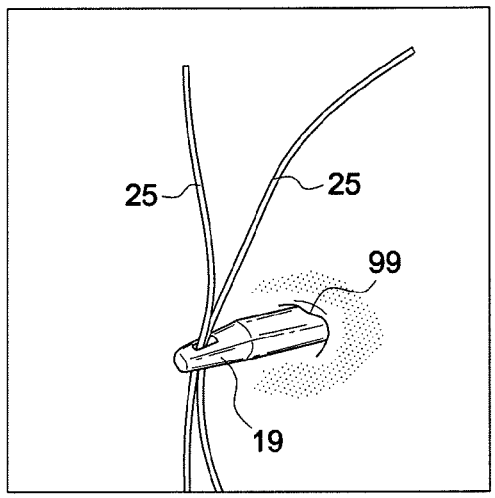
Figure 10:
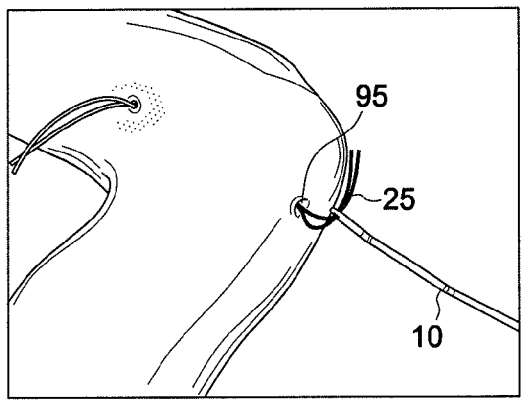

FIGS. 9 and 10: The suture 25 from the passport cannula 22 is passed into the eyelet 19a and the obturator 10 is pulled out the anterior portal 95 to deliver sutures 25.

Figure 11:
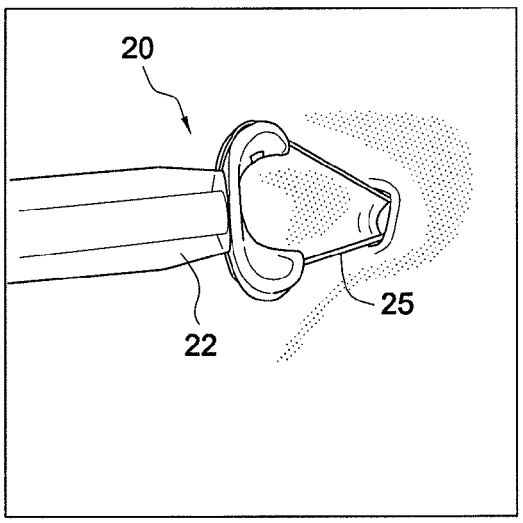
Figure 12:
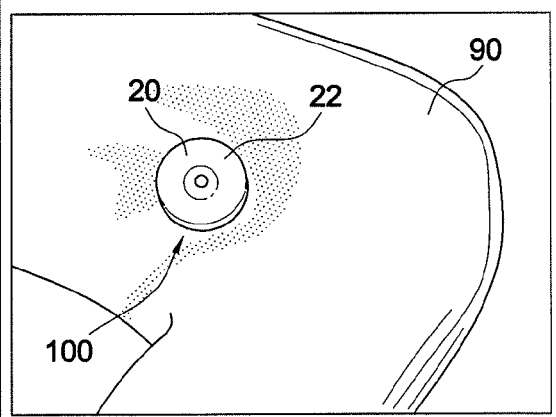

FIGS. 11 and 12: The sutures 25 are pulled to deliver the PassPort™ Button cannula 22 into the posterior portal 100.

Figure 13:
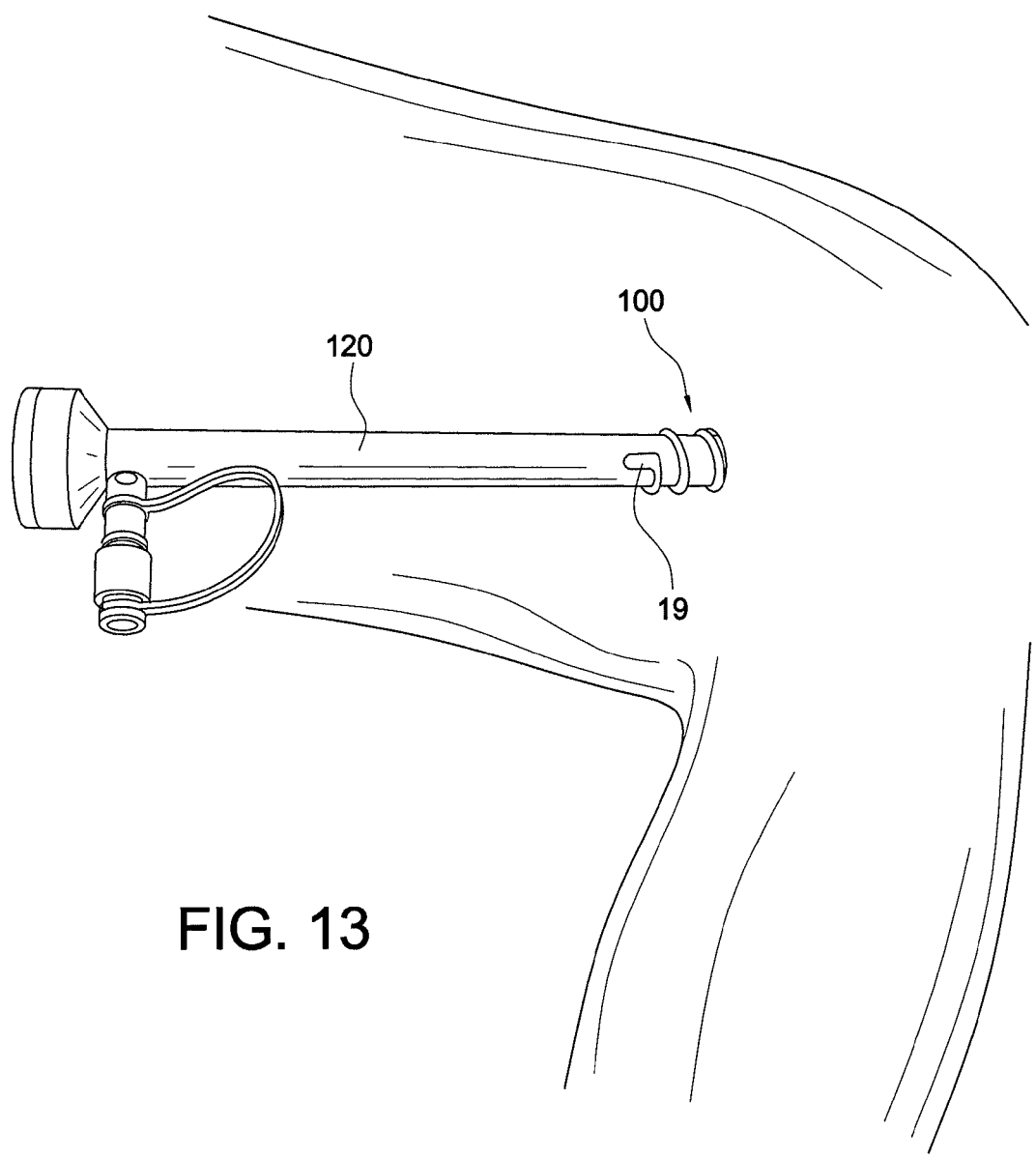
FIG. 13 illustrates the formation of a posterior knee portal and passage of a straight cannula with the obturator of FIGS. 1-3 and according to an exemplary embodiment of the present invention.

FIG. 13: Alternatively, a rigid cannula 120 may be passed over the tapered tip 19 of the obturator 10 and guided into the joint.

FIGS. 14-26 illustrate yet another embodiment of the present invention according to which the formation of posterior knee portal 100 is conducted through the medial knee portal (and not through the anterior knee portal, as detailed above). As in the previously-described embodiment, cannula passage includes passing a straight cannula or a modified PassPort™ Button cannula (which may comprise multiple flexible strands passed through at least one of the flanges of the cannula).

Figure 14:
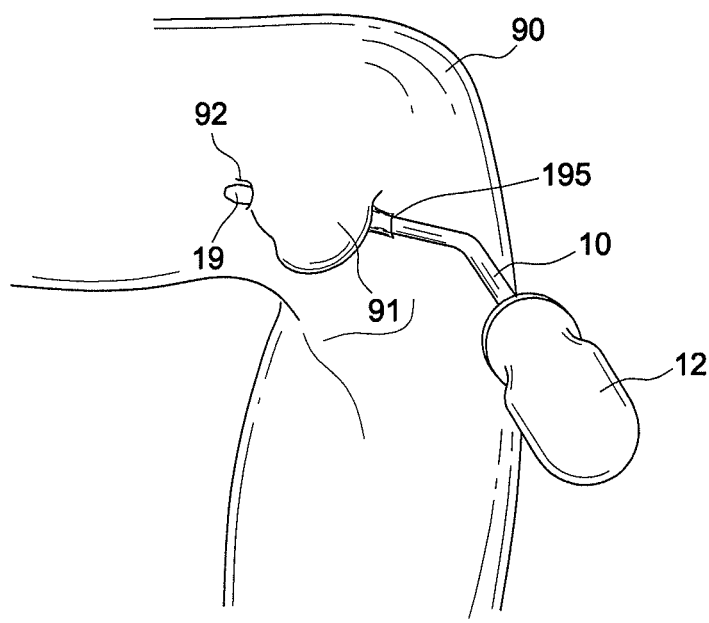
FIGS. 14-17 illustrate the formation of a posterior knee portal with the obturator of the present invention and according to another embodiment of the present invention (with the obturator placed in the medial portal for posteriomedial portal creation).

FIG. 14: The obturator 10 is placed in the medial portal 195 of knee 90 for posteromedial portal creation.

Figure 15:
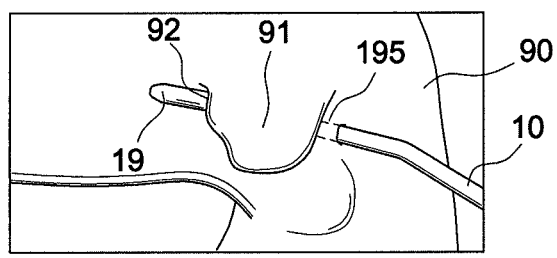

FIG. 15: The tip 19 of the obturator 10 is placed around femoral condyle 91 and against the capsule (not shown) until the tip 19 can be palpated or seen tenting the skin 92.

Figure 16:
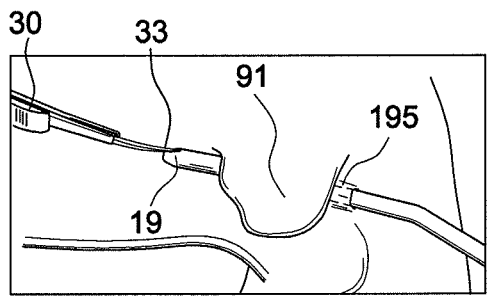
Figure 17:
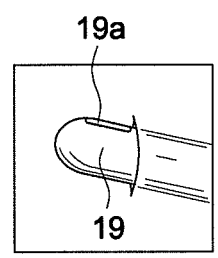

FIGS. 16 and 17: An incision 33 is made over the obturator 10 with a cutting instrument 30 (for example, scalpel 30), exposing the tip 19 (FIG. 17). The incision 33 should be made at a safe distance from neurovascular structures.

Figure 18:
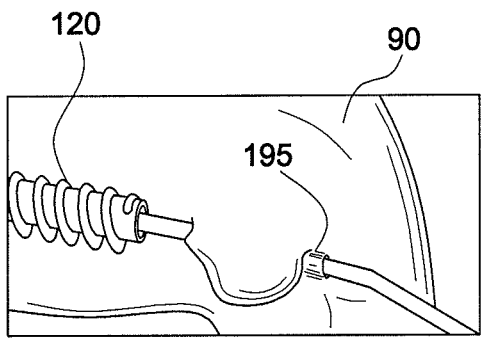
FIGS. 18 and 19 illustrate a threaded cannula placed over the obturator of FIG. 17.
Figure 19:
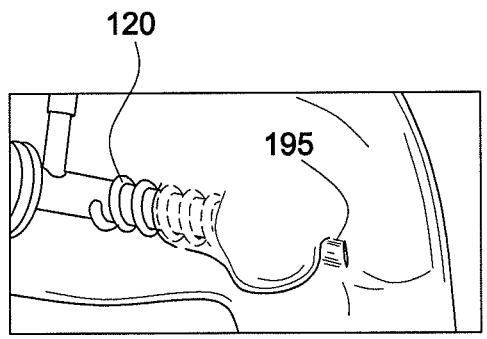

FIGS. 18 and 19: Plastic Cannula Option: A threaded cannula 120 can be placed over the obturator 10 from outside/in. It may be necessary to open the incision 33 or capsule further before introducing a larger diameter cannula. Alternatively, an open cannula may be used and slid down the side of the knee obturator 10 during insertion.

Figure 20:
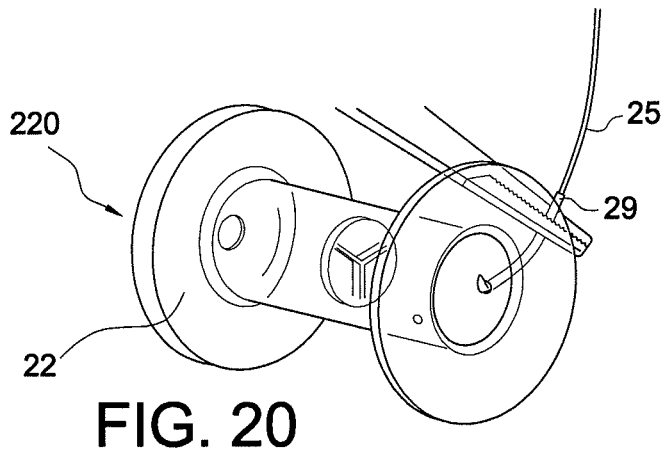
FIGS. 20-22 illustrate perspective views of a PassPort™ Button cannula with flexible strand passed through a "neck" for use with the obturator of the present invention, and according to another embodiment of the present invention (with two or more flexible strands passed through the neck).
Figure 22:
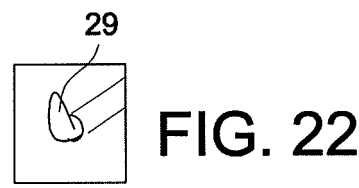
Figure 21:
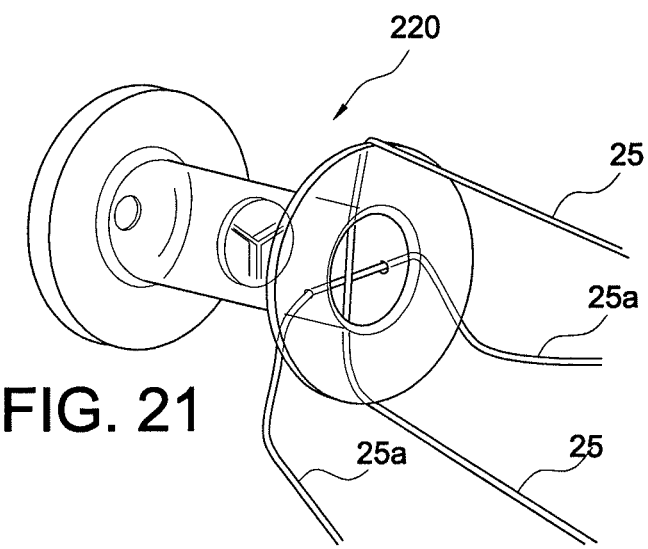

FIGS. 20-22: PassPort™ Button Cannula Option: For PassPort™ Button cannula insertion, at least two flexible strands, for example, two or more #2 FiberWire® sutures 25, 25a, can be placed into the "neck" of the cannula 220 using a curved needle 29 (FIG. 22). These flexible strands can be used as traction sutures to pull the cannula 220 into the knee 90.

Figure 23:
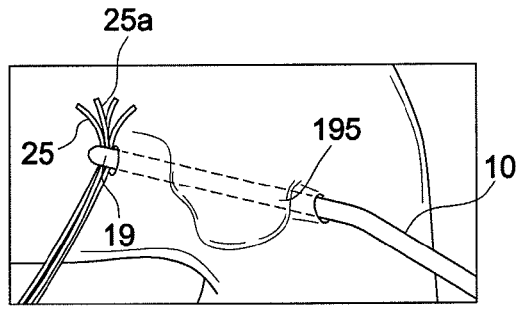
FIGS. 23-26 illustrate subsequent steps of a method of passing the cannula of FIGS. 20-22 with the obturator of the present invention, and according to another exemplary embodiment of the present invention.
Figure 24:
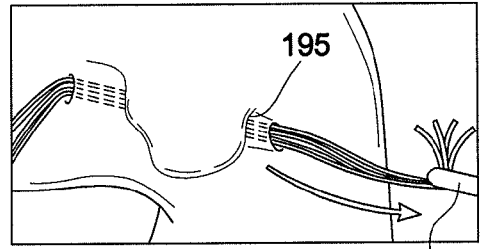

FIGS. 23 and 24: The PassPort™ sutures 25, 25a are placed into the knee obturator eyelet 19a and pulled through the knee 90.

Figure 25:
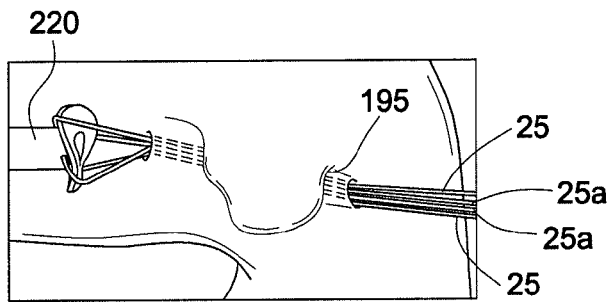
Figure 26:
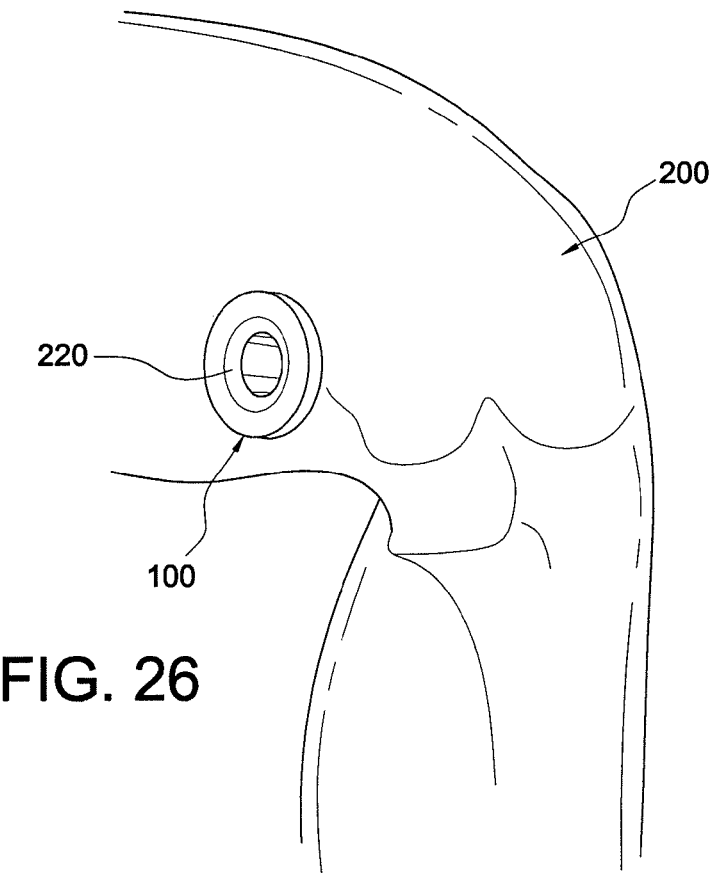

FIGS. 25 and 26: The PassPort™ Button cannula 220 is pulled into place. It may be necessary to open the incision or capsule further before introducing the PassPort™ Button cannula 220.

The knee obturator 10 detailed above has a curvature that is specially designed to simplify the location and creation of posterior knee portals, as well as introduction of a cannula. Posterior portals are often necessary for several common procedures such as loose body removal, PCL reconstruction, meniscal root avulsion repair and popliteal cyst debridement. Current outside/in techniques can be time-consuming and put posterior structures at risk of damage with sharp spinal needles and scalpels. The knee obturator 10 allows surgeons to quickly create the portal from the inside/out. The unique curvature 16 fits around the cruciate ligaments and around the back of the femoral condyles. The tapered eyelet tip 19 facilitates insertion of a PassPort™ Button cannula 20, 220 with one or more traction sutures 25, 25a or acts as a switching stick for cannula insertion.

The knee obturator 10 of the present invention may be employed to create posterior knee portals as part of various arthroscopic surgeries, for example, PCL reconstruction, meniscal repairs such as meniscal root avulsion repair and popliteal cyst debridement, and loose body removal, among many others. The knee obturator 10 may be provided together with one or more cannulas 20, 220 as a kit, to aid the surgeon during arthroscopic surgery. The kit may also include an elevator (for example, an articulating paddle elevator) and/or additional straight open cannulas which may be partially or fully threaded.

The present invention provides at least the following novel features that differentiate it over the existing prior art:

1) Shape of obturator allows entry from an anterior knee portal, gets around structures within the knee and exits the back of the knee in the appropriate position for a posterior-medial or posterior-lateral portal, allowing a guide for cutting and cannula placement.

2) Eyelet in obturator allows passage of suture to pull a cannula into place.

3) Suture in passport cannula allows pulling into place versus pushing.

4) Fit between obturator tip and cannula allows passage of cannula over the obturator and into the joint.

The at least one flexible strand 25, 25a may be high-strength sutures, such as the high strength suture sold by Arthrex, Inc. of Naples, Fla. under the registered tradename TigerWire® or FiberWire®, which is disclosed and claimed in U.S. Pat. No. 6,716,234, the entire disclosure of which is incorporated by reference in its entirety herewith. FiberWire® suture is formed of an advanced, high-strength fiber material, namely ultrahigh molecular weight polyethylene (UHMWPE), sold under the tradenames Spectra (Honeywell) and Dyneema (DSM), braided with at least one other fiber, natural or synthetic, to form lengths of suture material. The preferred FiberWire® suture includes a core within a hollow braided construct, the core being a twisted yarn of UHMWPE.

The flexible strands 25, 25a may be also formed of suture tape or a suture chain. The suture tapes may have the same, uniform width or may have different widths, and may comprise the same or different materials.

While the present invention is described herein with reference to illustrative embodiments for particular applications, it should be understood that the invention is not limited thereto. Those having ordinary skill in the art and access to the teachings provided herein will recognize additional modifications, applications, embodiments and substitution of equivalents all fall within the scope of the invention.

What is claimed is:

1. A curved obturator comprising: a handle; and a shaft attached to the handle and comprising a substantially curved portion and a substantially straight portion located between the substantially curved portion and the handle, and the substantially curved portion includes 3 curves and is adapted to follow a curvature of an anatomy of a knee such that the shaft avoids knee structures and preserves the knee structures intact during a surgical procedure.

2. A curved obturator comprising: a handle; and a shaft fixedly attached to the handle, the shaft configured as a solid rod and comprising a substantially curved portion comprising 3 curves shaped to follow a curvature of a medial femoral condyle or a lateral femoral condyle such that the shaft avoids knee structures and preserves the knee structures intact during a surgical procedure, and such that the shaft is configured to exit at a posterior-medial or posterior-lateral side of the knee when the shaft is inserted through an anterior portal.

3. The curved obturator of claim 1, wherein the shaft further comprises a substantially straight portion located between the substantially curved portion and the handle.

4. The curved obturator of claim 1, wherein the substantially curved portion terminates in a tapered tip with an eyelet to allow passage of at least one flexible strand therethrough.

5. The curved obturator of claim 4, wherein the at least one flexible strand is attached to a cannula.

6. The curved obturator of claim 5, wherein the cannula comprises an elongated body having a longitudinal axis, a first end and a second opposed end, a first flexible flange integral with the first end and a second flexible flange integral with the second end, wherein the first and second flexible flanges are oriented about perpendicular to the longitudinal axis of the elongated body, and wherein the at least one flexible strand is passed through the elongated body or one of the first and second flanges of the cannula.

7. The curved obturator of claim 3, wherein the substantially straight portion is about twice the length of the substantially curved portion.

8. The curved obturator of claim 1, wherein the substantially curved portion is adapted to fit around a) cruciate ligaments, b) against a capsule, and c) between the medial and lateral femoral condyles.

9. The curved obturator of claim 3, wherein the substantially curved portion is adapted to fit around a) cruciate ligaments, b) against a capsule, and c) between the medial and lateral femoral condyles.

10. The curved obturator of claim 1, wherein the shaft and the handle are fixed from moving relative to one another.

11. The curved obturator of claim 1, wherein the curved portion includes a first curve that curves outwardly from a straight portion of the shaft by a first distance, a second curve that further curves outwardly by a second distance, and a third curve that further curves outwardly by a third distance.

12. The curved obturator of claim 11, wherein the second distance is smaller than the first distance or the third distance.

13. A kit for posterior knee portal formation for arthroscopic surgery, comprising: the curved knee obturator according to claim 1, wherein the substantially curved portion terminates in a tip with an eyelet adapted to allow at least one flexible strand to pass therethrough; and a cannula comprising an elongated body having a longitudinal axis, a first end and a second opposed end, a first flexible flange integral with the first end and a second flexible flange integral with the second end, wherein the first and second flexible flanges are oriented about perpendicular to the longitudinal axis of the body, and at least one flexible strand passing through the elongated body or through one of the first and second flanges of the cannula.

14. The kit of claim 13, further comprising a curved needle adapted to allow the at least one flexible strand to pass through the elongated body or through one of the first and second flanges of the cannula.

15. The kit of claim 13, wherein the at least one flexible strand is a traction suture that passes through the eyelet of the obturator and pulls the cannula into knee through the posterior knee portal.

16. A curved obturator comprising: a shaft comprising a substantially curved portion including 3 curves, the substantially curved portion adapted to follow a curvature of an anatomy of a knee such that the shaft avoids knee structures and preserves the knee structures intact during a surgical procedure; and the substantially curved portion terminating in a tapered tip and including an eyelet formed through the tapered tip.

* * * * *